United States Patent
Sakaguchi et al.

(10) Patent No.: US 9,820,536 B2
(45) Date of Patent: Nov. 21, 2017

(54) FASTENING MEMBER AND FASTENING SEGMENT

(75) Inventors: Satoru Sakaguchi, Kanonji-shi (JP); Tadato Oritani, Sagamihara-shi (JP)

(73) Assignees: UNICHARM CORPORATION, Ehime (JP); 3M INNOVATIVE PROPERTIES COMPANY, Minnesota ( * ) Notice: Subject to any disclaimer, the term of this patent is extended or adjusted under 35 U.S.C. 154(b) by 233 days.

(21) Appl. No.: 14/344,975

(22) PCT Filed: Sep. 14, 2012

(86) PCT No.: PCT/JP2012/073672
§ 371 (c)(1),
(2), (4) Date: Mar. 14, 2014

(87) PCT Pub. No.: WO2013/039219
PCT Pub. Date: Mar. 21, 2013

(65) Prior Publication Data
US 2014/0338159 A1    Nov. 20, 2014

(30) Foreign Application Priority Data
Sep. 16, 2011 (JP) ................................ 2011-203456

(51) Int. Cl.
*A44B 18/00* (2006.01)
*A61F 13/62* (2006.01)
*A61F 13/56* (2006.01)

(52) U.S. Cl.
CPC ...... *A44B 18/0015* (2013.01); *A44B 18/0019* (2013.01); *A61F 13/5622* (2013.01);
(Continued)

(58) Field of Classification Search
CPC ............ A44B 18/0015; A44B 18/0019; A61F 13/625; A61F 13/5622; A61F 13/5638; A61F 13/622; A61F 13/627
See application file for complete search history.

(56) References Cited

U.S. PATENT DOCUMENTS 6,210,389 B1    4/2001 Long et al.
2006/0293635 A1*  12/2006 Petersen ............... A61F 13/625
                                                      604/385.03

FOREIGN PATENT DOCUMENTS

JP    2002-017778 A    1/2002
JP    2002-065730 A    3/2002
(Continued)

OTHER PUBLICATIONS

Office Action dated Sep. 28, 2015, corresponding to Eurasian Patent Application No. 201400357.
(Continued)

*Primary Examiner* — Abigail Troy
(74) *Attorney, Agent, or Firm* — Hauptman Ham, LLP (57) ABSTRACT

Provided are a fastening member and a fastening piece for which an unpleasant texture and an incongruous appearance are significantly reduced, and that bring about an integrated feeling with the main body of a disposable article for wearing. A fastening segment includes a hook fastener and a base sheet. A hook height H1 of a hook is set to 45 μm to 150 μm, and a hook sheet thickness T2 is set to 45 μm to 75 μm. When in an L*a*b* color coordinate system, a color difference of L* is ΔL*, a color difference of a* is Δa*, and a color difference of b* is Δb*, a color difference ΔE between the hook fastener and the base sheet calculated using the ΔL*, the Δa* and the Δb*, is less than 5.5.

21 Claims, 7 Drawing Sheets

(52) U.S. Cl.
CPC ........ *A61F 13/5638* (2013.01); *A61F 13/622* (2013.01); *A61F 13/625* (2013.01); *A61F 13/627* (2013.01); *Y10T 24/27* (2015.01)

(56) References Cited

FOREIGN PATENT DOCUMENTS

| JP | 2004-261354 A | 9/2004 |
|---|---|---|
| JP | 2005-040231 A | 2/2005 |
| JP | 2005-514976 A | 5/2005 |
| JP | 2011-072340 A | 4/2011 |

OTHER PUBLICATIONS

Office Action dated Sep. 29, 2015, corresponding to Japanese Patent Application No. 2011-203456.
Office Action in Egyptian Application No. 2014030396, dated Jan. 6, 2016.
Office Action in EA Application No. 201400357, dated Mar. 31, 2016.
Extended European Search Report dated Apr. 22, 2015, corresponding to European patent application No. 12831189.1.
Office Action dated Dec. 22, 2014, corresponding to Chinese patent application No. 201280044899.6.
International Search Report dated Oct. 9, 2012, in International Application No. PCT/JP2012/073672, filed Sep. 14, 2012.
Office Action in AU Patent Application No. 2012309375, dated May 5, 2016.
Office Action in EG Patent Application No. 2014030396 dated May 24, 2016.
Office Action in TW Patent Application No. 101133793, dated Jun. 4, 2016.
Office Action in AU Patent Application No. 2012309375, dated Oct. 20, 2016.

* cited by examiner

FASTENING MEMBER AND FASTENING SEGMENT

RELATED APPLICATIONS

The present application is a National Phase of International Application Number PCT/JP2012/073672, filed Sep. 14, 2012 and claims priority from Japanese Application Number 2011-203456, filed Sep. 16, 2011.

TECHNICAL FIELD

The present invention relates to a fastening member and a fastening segment provided in a wearing article that is won a human or a like.

BACKGROUND ART

Conventionally, as a disposal diaper which is a kind of a wearing article that is won a human or a like, an open-type disposal diaper and a pants-type disposal diaper have been extensively provided. The open-type disposal diaper includes a front waistline unit, a crotch unit, and a rear waistline unit, and is generally provided with a fastening member that detachably fastens the front waistline unit and the rear waistline unit, specifically, a hook fastener.

Further, the pants-type disposal diaper also has a hook fastener at one of joint portions between the front waistline unit and the rear waistline unit thereof.

For such a disposal diaper, there has been proposed a hook fastener having both superior softness and strong engaging force (for example, Patent Literature 1). Specifically, there has been disclosed a hook fastener in which a hook-side base has a thickness of about 0.04 mm to 0.13 mm, a hook has a height of about 0.1 mm to 1.3 mm, and the hook has a stiffness of about 0.01 mm to 0.1 N/9 mm (a loop stiffness value).

CITATION LIST

Patent Literature

[PTL 1] Japanese Unexamined Patent Application Publication No. 2005-40231 (Pages 5 to 6, FIG. 1)

SUMMARY OF INVENTION

Meanwhile, in recent years, demands of a user (a purchaser) for a disposal diaper are increased, and specifically, when an infant wears the disposal diaper, there is an increased awareness that parents would like to cause no burden to the skin of the infant or reduce a burden to the skin of the infant if possible.

However, even when applying the conventional fastening member as described above, since a hook fastener provided with a plurality of hooks causes a significant discomfort in touch and physical appearance as compared with other portions of a disposal diaper made of nonwoven fabric, it is not possible to completely solve the uneasiness of a user in recent years in which demands for a disposal diaper have been increased.

Therefore, the present invention has been achieved in view of the above-mentioned problems, and an object thereof is to provide a fastening member and a fastening segment, which is capable of significantly reducing a discomfort in touch and physical appearance and achieving a sense of unity with the body of the wearing article of a disposal diaper or a like.

As a result of earnest studies conducted by the inventor(s) of the present invention in order to solve the above-mentioned problems, it was gradually revealing that the existence of three factors by which the conventional fastening member (a hook fastener) causes a discomfort. Specifically, the three factors are (1) a sense of thickness of a hook fastener regarding touch of a number of hooks and a hook sheet provided with the number of hooks, (2) impression caused by directly having visual contact with a hook, and (3) a sense of unity between the hook sheet and a base sheet that the hook sheet is fixed.

Due to the three factors, a user of a wearing article (e.g., a disposal diaper) provided with the conventional fastening member has an impression that the fastening member causes a discomfort as compared with other portions (a nonwoven fabric and the like) of the disposal diaper.

More specifically, since the thickness of the fastening member is large, a user has an impression that the fastening member is "solid" or is "unfamiliar to the body". Further, by the height of the hook, a user has an impression that the hook is hard pointed. In addition, the difference in visual impression between the fastening member and other portions (the nonwoven fabric and the like) causes an impression that the fastening member is made of a material (e.g., plastic) different from a material constituting the disposal diaper.

Further, as a phenomenon frequently observed in some mothers after childbirth, it has been known that a mother in a non-ordinary state due to a change of hormone balance has high maternity. Since a mother in such a state has a subconscious that she would like to protect her own child (an infant) from an object giving out an impression of "solid" and an object giving out an impression of "pointed", it is also observed that she has an especially-strong discomfort or feeling of dislike for the fastening member as described above. For example, in the underwear of an infant, a tag and a seam are provided at the outer side of the underwear in order to prevent the tag and the seam from making contact with the skin of the infant. That is, it was learned that the hook sheet and the hook constituting the fastening member as described above can be recognized as just equivalents for a label and a seam by a mother.

The first feature of the present invention is summarized in that:

a fastening member (example, a hook fastener 110) for a wearing article has a plurality of hooks (a hooks 111) and a planar hook sheet (a hook sheet 112) that is provided with the plurality of hooks, comprising:

a height of the hook is 45 μm to 150 μm, a thickness of the hook sheet is 45 μm to 75 μm, and when in an L*a*b* color coordinate system, a color difference of L* is ΔL*, a color difference of a* is Δa*, and a color difference of b* is Δb*, a color difference ΔE between the fastening member and a base sheet provided on the wearing article, and is the fastening member is fixed, calculated using the ΔL*, the Δa* and the Δb*, is less than 5.5.

The second feature of the present invention is summarized in that:

a fastening segment comprising:

a fastening member has a plurality of hooks and a planar hook sheet that is provided with the plurality of hooks, a base sheet provided on the wearing article, and the fastening member is fixed, wherein:

a height of the hook is 45 μm to 150 μm, a thickness of the hook sheet is 45 μm to 75 μm, and when in an L*a*b* color coordinate system, a color difference of L* is ΔL*, a color difference of a* is Δa*, and a color difference of b* is Δb*, a color difference ΔE between the fastening member and the base sheet calculated using the ΔL*, the Δa* and the Δb*, is less than 5.5.

DESCRIPTION OF EMBODIMENTS

An embodiment of fastening member according to the present invention will be explained with reference to drawings. It is noted that in the following description of the drawings, identical or similar portions are assigned identical or similar references. However, it should be noted that the drawings are merely exemplary and ratios of each dimension differ from the actual ones.

Therefore, a specific dimension should be determined in view of the following description. Moreover, among the drawings, the respective dimensional relations or ratios may differ.

(1) Schematic Configuration of a Wearing Article

Figure 1:
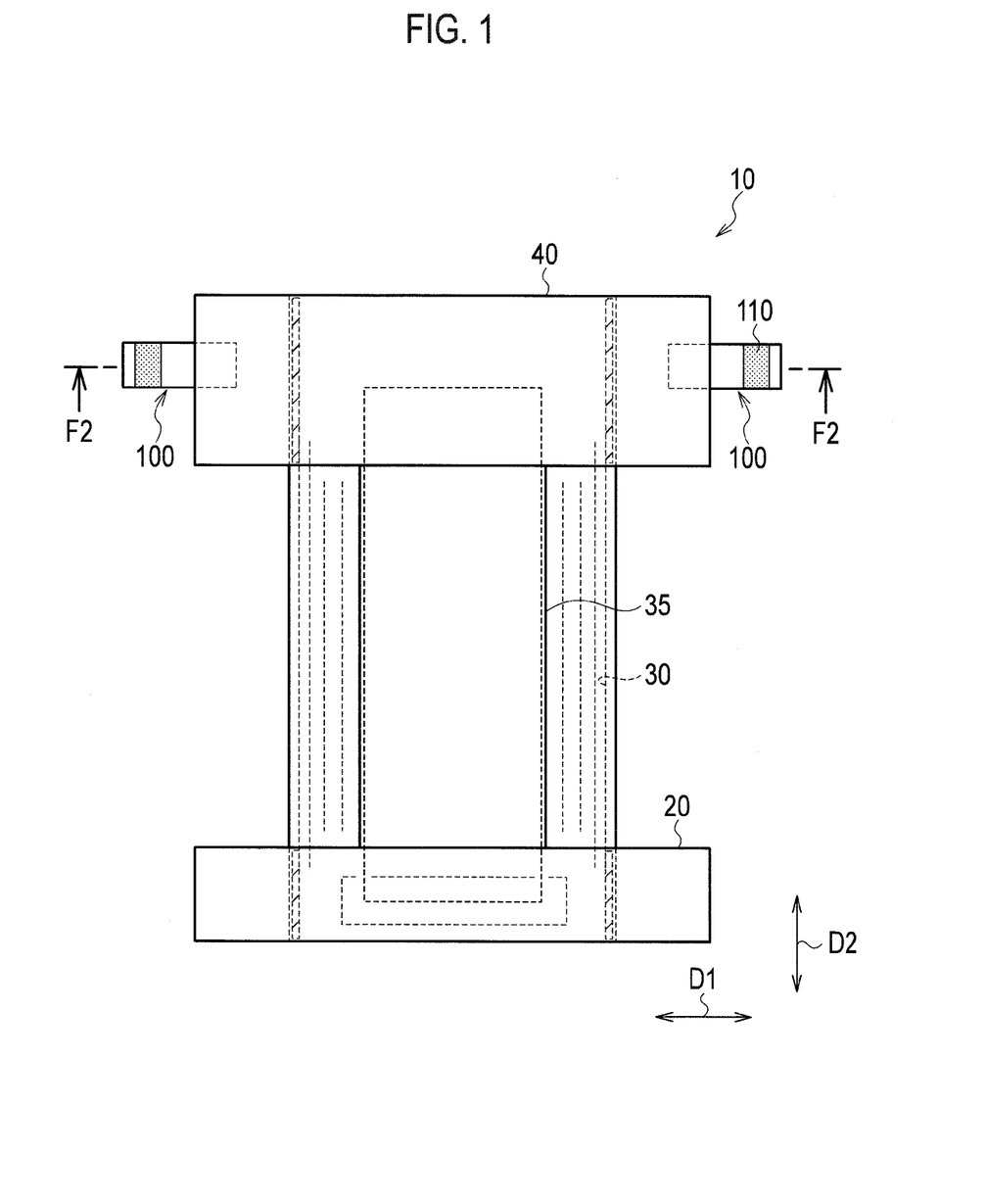
FIG. 1 is a plan view of a disposal diaper 10 according to an embodiment of the present invention.
Figure 2:
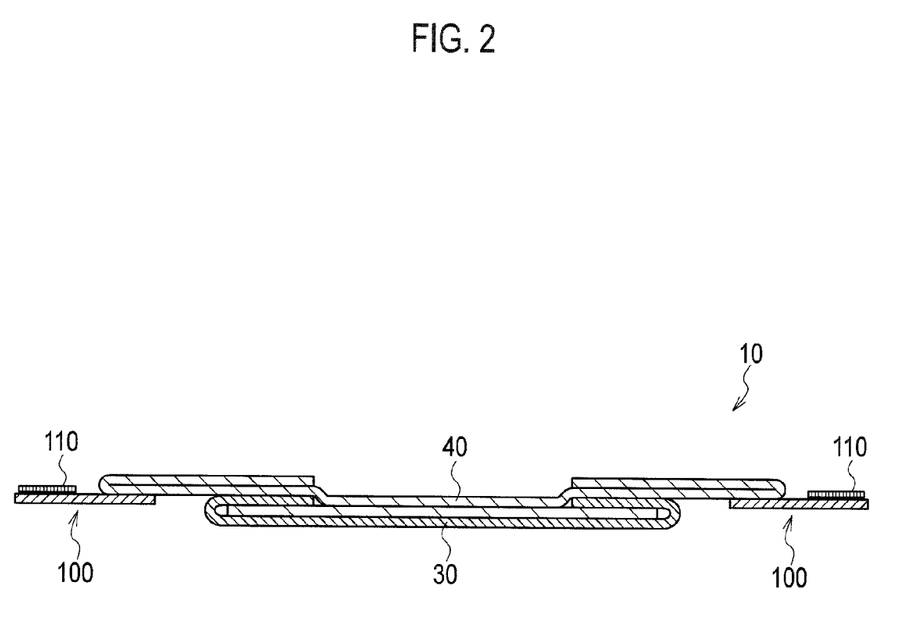
FIG. 2 is a cross-sectional view taken along line F2-F2 illustrated in FIG. 1.
Figure 3:
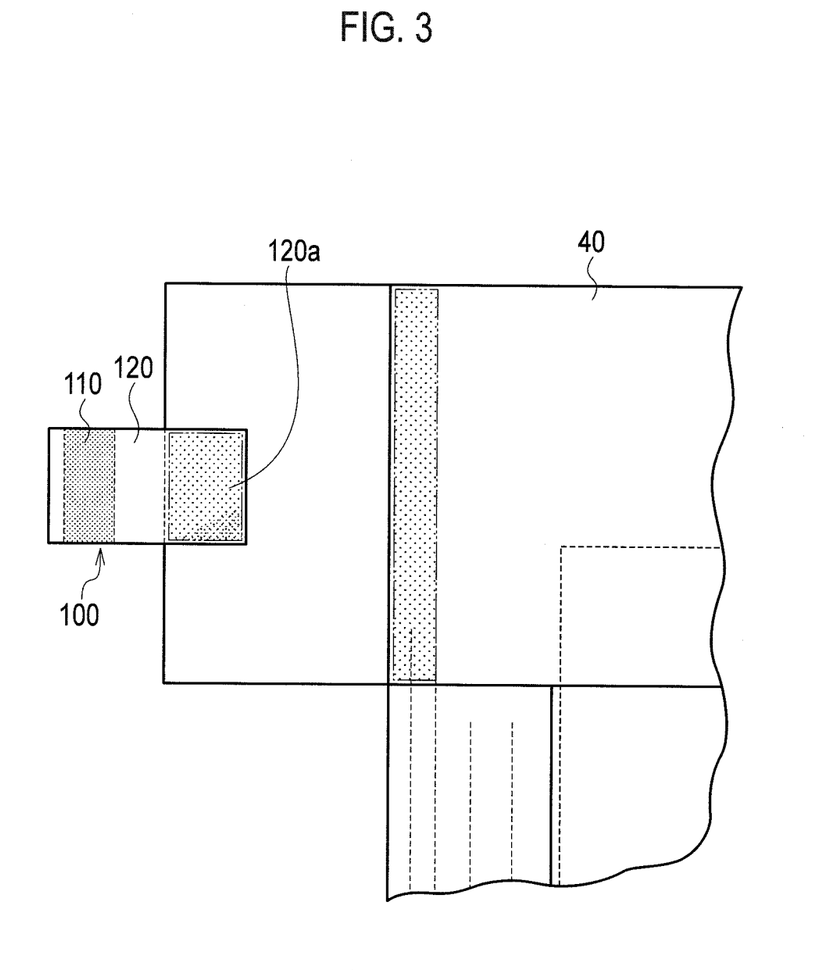
FIG. 3 is an enlarged view of a rear waistline unit provided in the disposal diaper 10 according to the embodiment of the present invention.

First, the schematic configuration of specifically a disposal diaper, a wearing article according to the present embodiment will be described with reference to FIG. 1 to FIG. 3. FIG. 1 is a plan view of a disposal diaper 10. FIG. 2 is a cross-sectional view taken along line F2-F2 illustrated in FIG. 1. FIG. 3 is an enlarged view of a rear waistline unit provided in the disposal diaper 10.

As illustrated in FIG. 1 to FIG. 3, the disposal diaper 10 is an open-type disposal diaper including a front waistline unit 20, a crotch unit 30, and a rear waistline unit 40. The crotch unit 30 is provided with an absorber 35 extending along the longitudinal direction D2 of the disposal diaper 10, configured to absorb a bodily waste such as urine.

The front waistline unit 20 and the rear waistline unit 40 are made of hydrophobic nonwoven fabric and the like including spunbond-meltblown-spunbond (SMS) nonwoven fabric, spunbond (SB) nonwoven fabric, and point bond nonwoven fabric. Further, the absorber 35 is provided between a liquid-permeable surface sheet and a liquid-impermeable back sheet. In addition, the basic configuration of the disposal diaper 10 is approximately the same as that of the conventional open-type disposal diaper, and for example, is approximately the same as that of a disposal diaper disclosed in JP-A-2002-65730.

The disposal diaper 10 is provided with a fastening segment 100 configured to detachably fasten the front waistline unit 20 and the rear waistline unit 40. The fastening segment 100 includes a hook fastener 110 engaged with the front waistline unit 20 of the disposal diaper 10, and a base sheet which the hook fastener 110 is mounted.

The hook fastener 110 includes a plurality of hooks 111 and a hook sheet 112 for supporting the plurality of hooks 111. The hook fastener 110 is mounted on the base sheet 120 which is provided on the disposal diaper 10. In the present embodiment, the hook fastener 100 constitutes a fastening member.

The hook fastener 110 is provided at a part of the surface of the base sheet 120. The base sheet 120 may be configured to be expandable along the width direction D1 of the disposal diaper 10.

In addition, the base sheet 120 may be provided separately from an element constituting the body of the disposal diaper 10 and adhere to the rear waistline unit 40 by a joint portion 120a as with the present embodiment, or may directly extend from the absorber 35 in the rear waistline unit 40 without using a side flap. Further, the hook fastener 110 may be provided on the entire surface of the base sheet 120.

(2) Shape of the Fastening Member

Figure 4:
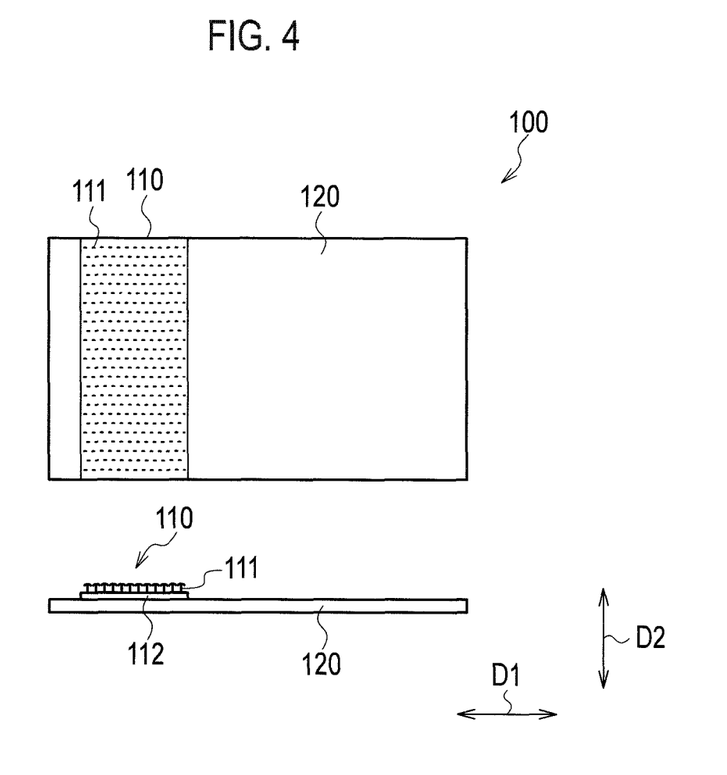
FIG. 4 is a monolithic plan and side view of a fastening segment 100 according to the embodiment of the present invention.
Figure 5:
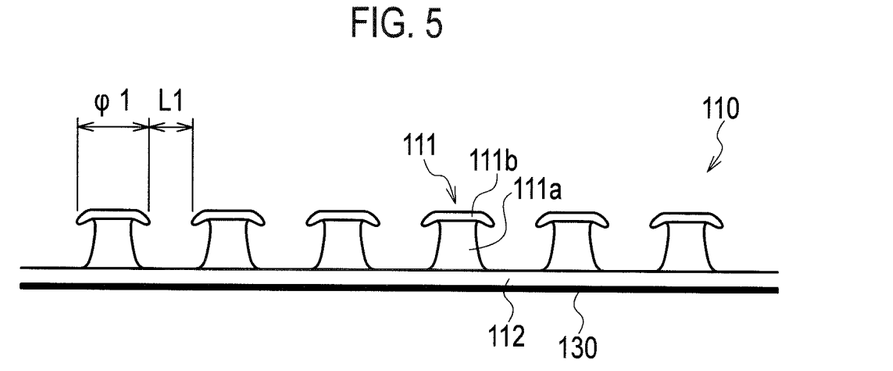
FIG. 5 is an enlarged side view of a hook fastener 110 according to the embodiment of the present invention.
Figure 6:
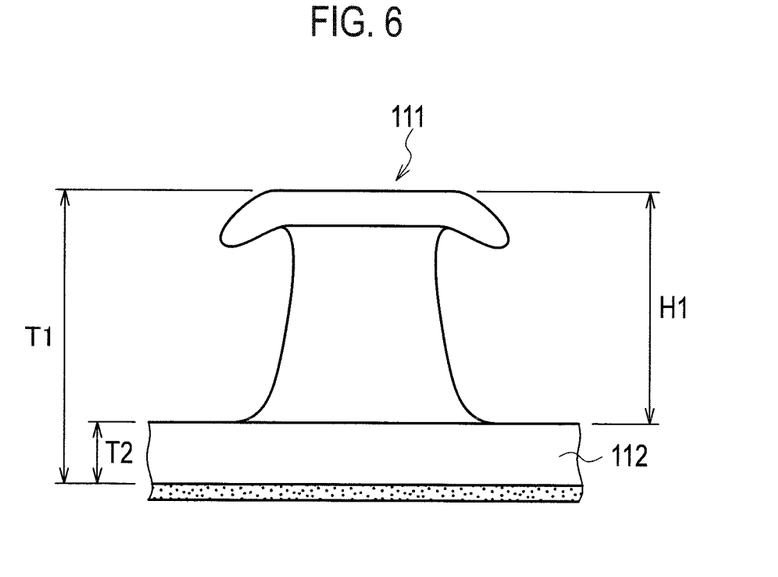
FIG. 6 is a side view of a hook 111 constituting the hook fastener 110 according to the embodiment of the present invention.

Next, the shape of the hook fastener 110 constituting the fastening member in the present embodiment will be described with reference to FIG. 4 to FIG. 6. FIG. 4 is a monolithic plan and side view of the fastening segment 100 includes the hook fastener 110. FIG. 5 is an enlarged side view of the hook fastener 110. FIG. 6 is a side view of a hook constituting the hook fastener 110.

As illustrated in FIG. 4 to FIG. 6, the hook fastener 110 is provided at a part of the surface of the base sheet 120. Specifically, the hook fastener 110 is provided in an outer area in the width direction D1 of the base sheet 120.

The hook fastener 110 includes a plurality of hooks 111 engaged with the front waistline unit 20 of the disposal diaper 10. Specifically, the hook fastener 110 includes the plurality of hooks 111 arranged along the width direction D1 and the longitudinal direction D2. The hook fastener 110 is a male member of a hook fastener which is engageable with the front waistline unit 20 made of nonwoven fabric. The plurality of hooks 111 are erected from a hook sheet 112 having a flat plate shape. Further, in the present embodiment, the distance L1 between adjacent hooks 111 is set 120 pm to 300 μm.

Each hook 111 includes a pillar unit 111a and an umbrella unit 111b. The pillar unit 111a has a pillar portion erected from the hook sheet 112, and the umbrella unit 111b is provided at a tip end of the pillar unit 111a and has a hook diameter ϕ1 greater than a diameter of the pillar unit 111a. The umbrella unit 111b is configured to be inserted into a space between nonwoven fabrics constituting the front waistline unit 20 to engage with the nonwoven fabrics. When the umbrella unit 111b is elliptical, the hook diameter ϕ1 is the length along the longitudinal direction of the umbrella unit 111b. In addition, the hook 111 may be engaged with a female member of the hook fastener.

On the back surface of the hook sheet 112 (a surface not provided with the hook 111), an adhesive layer 130 for fixing the hook sheet 112 to the base sheet 120, is provided.

As a material constituting the hook fastener 110, a material well known in the art can be used. For example, it is possible to use olefin such as polyethylene and polypropylene, polyester such as polyethylene terephthalate, and the like. Otherwise, it may be possible to use a mixture of these materials or a material including a foaming agent added thereto.

As a material constituting the base sheet 120, nonwoven fabric is mainly used, which is manufactured by a manufacturing method such as spunbond (SB) or spunbond-meltblown-spunbond (SMS), point bond, and air-through. In addition, SMS nonwoven fabric may have a two- or four-layer structure, other than a three-layer structure, in order to control the strength and flexibility thereof.

The entire weight of the nonwoven fabric constituting the base sheet 120 is 10 g/m² to 100 g/m². Further, the entire thickness of the nonwoven fabric is 50 µm to 600 µm. The base sheet 120 may be configured to overlap single sheet of a nonwoven fabric sheet or a plurality of nonwoven sheet (2 or 3 sheets). Per weight of the nonwoven fabric sheet is 10 to 80 g/m², preferably 20 to 65 g/m², further preferably 25 to 45 g/m². The entire thickness of the base sheet 120 is, as described above, 50 µm to 600 µm, preferably the thickness is 150 µm to 500 µm.

When using the nonwoven fabric to the base sheet 120, by using the above mentioned range, the base sheet 120 of the nonwoven fabric which is possible to ensure adequate flexibility in comparison with the hook fastener 110, and which can be secured to the required strength and ease handling of as an element to stop the hook fastener 110 to the disposal diaper 10, and which may be not feel a sense of foreign matter, if a thickness of impression, compared with the hook fastener 110.

When the basis weight greater than 100 g/m², since the bulk of the fibers of the nonwoven fabric is increased, there is a further need to increase a thermal fusion point for entangling and fixing the fibers to be configured, and, the bending stiffness of the base sheet 120 stand out compared to the bending stiffness of the hook fastener 110. In addition, if the thickness exceeds 600 µm, since they give the user the feeling of a foreign body from feeling the thickness of the base sheet 120 itself (change from impression of fabric feeling to impression of feeling plastic), affect the sense of unity with the hook fastener 110 and the base sheet 120.

Further, when the basis weight smaller than 10 g/m², the base sheet 120 is attached the hook fastener 110 is difficult to ensure sufficient strength, and if thickness is less than 50 µm, when stopping to the disposable diapers 10 the hook fastener 110 or removing the hook fastener 110 from the disposable diapers 10, it becomes difficult to operate its attachment and removal.

In addition, when as these, the base sheet 120 composed of the nonwoven fabric, it is also possible to overlap a plurality of nonwoven fabric. In this case, per sheet basis weight is lower than the overlap a higher basis weight nonwoven fabric of one sheet (when overlaid a plurality of sheet, more preferably may be using a nonwoven basis weight of the above mentioned range), dividing into a plurality of sheet of two sheets or three sheets and than overlapping, thereby can be equal to less than 600 µm the thickness of the whole, to realize a more balanced manner by which the above-mentioned aims. Note, the thickness of the nonwoven fabric was measured using a thickness tester (Tester for Tester Sangyo., Ltd.) which the shape of the measurement terminal is a circular shape, and the load is 1.23N.

Further, when the base sheet 120 configured by a plurality of sheet, each other between the sheets can be joined together by various means, preferably its applying a line (including spiral like) or a point a hot melt adhesive, thereby its be fixed between the sheets of each other is preferred from the viewpoint of flexibility and productivity.

The height H1 (see FIG. 6) of the hook is set 45 µm to 150 µm. The thickness T2 of the hook sheet is set 45 µm to 75 µm. The total thickness T1, which is the hook 111 and the hook sheet 112, is preferably 115 µm to 200 µm from a test results described below.

In addition, if the hook height H1 is set to be larger than 150 µm, it is easy to visibly recognize the presence of the hook and a user may have an impression that the hook fastener 110 is visibly pointed, which is not preferable. Further, if the hook height H1 is set to be smaller than 45 µm, since it may not be possible to sufficiently exhibit the original function by which the hook fastener 110 is engaged with other sheets (the female member of the hook fastener or the like), desired engagement strength cannot be ensured.

Moreover, when the L*a*b* color coordinate system, a color difference of L* is $\Delta L^*$, a color difference of a* is $\Delta a^*$, and a color difference of b* is $\Delta b^*$, a color difference $\Delta E$ between the hook fastener 110 and the base sheet 120 calculated using the $\Delta L^*$, the $\Delta a^*$ and the $\Delta b^*$, is set to less than 5.5.

Note, $\Delta E$ can be calculated by [Math 1].

$$\Delta E = \sqrt{\Delta L^{*2} + \Delta a^{*2} + \Delta b^{*2}}$$ [Math. 1]

Further, a light transmittance of from the tip side of the hook 111 to the base sheet 120 side, is preferably 60 to 85%.

In addition, an accumulated value, which is calculated by a standard deviation (MMD) of an average coefficient of friction (MIU) of the hook fastener 110, and an average deviation of the average coefficient of friction (SMD), is preferably 0.10 to 0.45.

Moreover, according to the present embodiment, a bending stiffness of the hook fastener 110 in the width direction D1 (the first direction) along the surface of the hook fastener 110 and a bending stiffness of the hook fastener 110 in the longitudinal direction D2 (the second direction) along the surface of the hook fastener 110 while being perpendicular to the width direction D1 are preferably equal to or less than 0.142 gf·cm²/cm, further preferably equal to or less than 0.072 gf·cm²/cm. In the present embodiment, the first direction is a direction in which the distance between the hooks is minimized, and the second direction is a direction perpendicular to the first direction.

(3) Example

Next, an example of the present invention will be described. The table 1 shows the test results and the schematic configuration of the fastening member in the example 1 to the example 6, and the fastening member in a comparative example 1 to a comparative example 3 (Hereinafter abbreviated to examples and the comparative examples as appropriate).

TABLE 1

| | HOOK HEIGHT H1 (μm) | HOOK SHEET THICK-NESS T2 (μm) | TOTAL THICK-NESS T1 (μm) | DISTANCE BETWEEN HOOKS L1 (μm) | TEST RESULTS ||||||
|---|---|---|---|---|---|---|---|---|---|---|
| | | | | | FABRIC FEELING | ENGAGE-ABILITY | COLOR DIFFERENCE | LIGHT TRANS-MITTANCE | BENDING STIFFNESS | SURFACE FRACTION PROPERTY |
| EX. 1 | 150 | 50 | 200 | 120 | OK | OK | OK | OK | OK | OK |
| EX. 2 | 120 | 45 | 165 | 300 | OK | OK | OK | OK | OK | OK |
| EX. 3 | 90 | 75 | 165 | 180 | OK | OK | — | — | OK | — |
| EX. 4 | 45 | 70 | 115 | 160 | OK | OK | — | OK | — | — |
| EX. 5 | 135 | 65 | 200 | 150 | OK | OK | — | OK | — | — |
| EX. 6 | 90 | 45 | 135 | 200 | OK | OK | — | NG | — | — |
| COMPARATIVE EX. 1 | 300 | 105 | 405 | 165 | NG | OK | OK | — | NG | NG |
| COMPARATIVE EX. 2 | 100 | 100 | 200 | 505 | NG | NG | — | — | — | — |
| COMPARATIVE EX. 3 | 45 | 85 | 130 | 120 | NG | OK | — | NG | NG | — |

※ "—" in the test results indicates that no test has been conducted.

As shown in Table 1, in a fabric feeling, a consistency engagement, a color difference, a light transmittance, a bending stiffness, and a surface friction characteristics are tested using the hook height H1 and a plurality of fastening members (the hook fasteners) that a hook sheet thickness T2 is different.

The following describes details of the measurement methods and the test results in each test.

(3.1) The Fabric Feeling and the Consistency Engagement

The hook height H1 of the fastening member, the hook sheet thickness T2 and the Total thickness T1 are calculated by measuring a sample in the each example and the each comparative example under no applied pressure. A measurement environment is that the temperature is 20±2° C., the relative humidity is 65±5%, and a microscope (VHX-900 manufactured by Keyence Corporation) is used as a measurement device.

First, an enlarged image of the section of the sample is obtained, and Samples with a known dimension are overlaid on the image and then displayed. A scale of the microscope is adjusted according to the enlarged image and the height and thickness of the sample is measured. The above-mentioned this operation is performed ten times, and an average value of heights and thicknesses obtained for ten times is an obtained value.

The test of "the fabric feeling" which is observed the samples (a square base sheet 120 of 50 mm×50 mm, a square hook fastener 110 of 30 mm×30 mm to the center of the base sheet 120) from the hook 111 side of the hook fastener 110 by the observer (subject number 50), and which is whether or not the impression such as fabric, conducted a sensitive evaluation by the following five step. The ratio of number of evaluation in (1) or (2) was accepted as YES (OK) a sample of more than 60%.

(1) Accepted a impression of same texture and feeling of fabric (2) Accepted a impression of approximately same texture and feeling fabric (3) No opinion (4) Accepted a impression of slightly different image and sense of discomfort (5) Accepted a impression of very different image and sense of discomfort Further, the test of "the consistency engagement" is measured by using a tester autograph (Shimadzu Corporation, AG-X10plus). Specifically, the hook fastener 110 and the base sheet 120 are prepared respectively the samples (a measurement result is 30 mm width if size can be cut, a values calculated per 30 mm width if size can not be cut). A sample that was cut in a size large than the hook fastener 110, it prepared on the member of a target position fastened the hook fastener 110.

A cylindrical roller which is moved along the main direction of detachable of the hook fastener 110 at a speed of 5 mm/min, and which is crimped the each sample. The roller is weight 2,000 g, diameter 95 mm, width 45 mm, and a thickness of a surface is the durometer hardness A prescribed in JIS K6253 of about 6 mm, and the surface is covered rubber of 80±5, and the roller was used to the surface without irregularities.

Next, the samples were crimped is set to the tester autograph. It was measured an engaging force (N/30mm) of the samples in the case where a pulling speed 300 mm/min. At this time, a pulling direction is set so that the surface of the hook fastener 110 is angle of 135° with respect to a surface of member in the target position that fastened the hook fastener 110. If the measured value of the measurement conditions is less than 0.2N/30 mm, the engagement force is determines that insufficient. If the measured value is greater than 0.2N/30mm, the engagement force is determines that Yes (OK).

(3.2) Color Difference (The L*a*b* Color Coordinate System)

An "L*" and "a*" and "b*" values of the hook fastener 110, and An "L*" and "a*" and "b*" values of the adjacent base sheet 120 to the hook fastener 110 are measured. Specifically, the measurement was conducted on the surface side of the hook 111. That is, the measurement was conducted on the surface the hook fastener 110 is opposed to an observer.

Coordinates L, a, b, was measured using a colorimeter (Minolta mode CR-300). More specifically, On the standard white plate, it are placed in the sequence the base sheet 120 (to above the mounting surface of the hook fastener 110) and the hook fastener 110 (to above the hook 111 side). The size of the hook fastener 110 is smaller than the size of the base sheet 120. Measurement (Measurement (1)) was measured the "L*" and "a*" and "b*" values at a position where only the base sheet 120 is present. In addition, measurement (Measurement (2)) was the "L*" and "a*" and "b*" values at a position where the hook fastener 110 and the base sheet 120 are exists in each overlapping state.

Next, ΔE (see Formula 1) was calculated using the "L*" and "a*" and "b*" values obtained in the Measurement (1) and the "L*" and "a*" and "b*" values obtained in the Measurement (2).

The table 2 shows the measurement results of the example 1, example 2 and the comparative example 1. As shown in the table 2, even in the same embodiment, the test was conducted a plurality of sample changing the color of the base sheet 120.

described above. The reason "sense of unity" of the comparative example 1 has become NG, is considered because it can not give the impression of fabric feeling, even if the reduced color difference (difference in visual), because the value of the hook height and the hook thickness is large.

In addition, according to the results from the observer interviews, if the color difference ΔE is less than 2.23, it has been found that with a determination that sense of the fabric feeling in the test of "fabric feeling" by 80% or more the observers. That is, the color difference ΔE is preferably less

TABLE 2

|  | FASTENER ATTACHMENT PIECE | L* | a* | b* | ΔL* | Δa* | Δb* | ΔE | COLOR DIFFERENCE IMPRESSION | SENSE OF UNITY |
|---|---|---|---|---|---|---|---|---|---|---|
| EX. 1 | WHITE | 93.99 | 0.62 | 1.20 | 0.02 | −0.16 | −0.24 | 0.29 | OK | OK |
|  | WHITE RED (PINK) GROUP-LIGHT | 89.45 | 4.98 | −1.47 | −0.13 | −0.07 | −0.49 | 0.51 | OK | OK |
|  | RED (PINK) GROUP INTERMEDIATE | 87.44 | 8.46 | −3.60 | 0.02 | −0.66 | 0.02 | 0.66 | OK | OK |
|  | BLUE GROUP LIGHT | 85.24 | −6.20 | −3.42 | 0.13 | 0.57 | 0.47 | 0.75 | OK | OK |
|  | BLUE GROUP INTERMEDIATE | 83.23 | −6.86 | −5.24 | 0.99 | 1.87 | 0.69 | 2.23 | OK | OK |
|  | RED (PINK) DARK | 83.14 | 11.86 | −6.50 | 0.52 | −2.23 | 0.94 | 2.48 | OK | OK |
|  | LIGHT BLUE | 84.95 | −7.72 | −11.54 | 1.81 | 0.00 | 2.71 | 3.26 | OK | OK |
|  | GREEN GROUP LIGHT | 86.62 | −10.80 | 10.93 | 0.15 | 1.83 | −3.75 | 4.18 | OK | OK |
|  | GREEN GROUP INTERMEDIATE | 84.19 | −13.09 | 12.25 | 0.52 | 3.57 | −5.17 | 5.30 | OK | NG |
|  | BLUE GROUP DARK | 77.61 | −5.36 | −12.22 | 3.45 | 3.42 | 4.54 | 6.65 | NG | NG |
|  | GREEN GROUP DARK | 78.74 | −18.19 | 14.52 | 2.50 | 8.91 | −11.09 | 14.44 | NG | NG |
| EX. 2 | WHITE | 94.35 | 0.58 | 1.07 | 0.38 | −0.20 | −0.37 | 0.57 | OK | OK |
|  | RED (PINK) GROUP LIGHT | 90.26 | 3.96 | −0.74 | 0.68 | −1.09 | 0.24 | 1.31 | OK | OK |
|  | RED (PINK) GROUP INTERMEDIATE | 88.73 | 6.94 | −2.80 | 1.31 | −2.18 | 0.82 | 2.67 | OK | OK |
|  | BLUE GROUP LIGHT | 87.31 | −4.51 | −3.04 | 2.20 | 2.26 | 0.85 | 3.27 | OK | OK |
|  | BLUE GROUP INTERMEDIATE | 85.77 | −5.05 | −3.86 | 3.53 | 3.48 | 1.97 | 5.33 | OK | OK |
|  | RED (PINK) GROUP DARK | 85.43 | 8.47 | −4.29 | 2.81 | −5.62 | 3.15 | 7.03 | NG | NG |
|  | GREEN GROUP LIGHT | 88.04 | −8.76 | 8.35 | 1.57 | 3.97 | −6.33 | 7.64 | NG | NG |
|  | GREEN GROUP INTERMEDIATE | 86.15 | −0.09 | 8.87 | 2.48 | 6.67 | −8.55 | 11.12 | NG | NG |
|  | BLUE GROUP DARK | 61.56 | −3.58 | −8.95 | 7.40 | 5.20 | 7.81 | 11.95 | NG | NG |
|  | GREEN GROUP DARK | 82.43 | −12.09 | 8.86 | 6.19 | 15.01 | −16.75 | 23.33 | NG | NG |
| COMPARATIVE EX. 1 | WHITE | 93.90 | 0.56 | 1.16 | −0.07 | −0.22 | −0.28 | 0.36 | OK | NG |
|  | RED (PINK) GROUP LIGHT | 90.07 | 4.08 | −1.17 | 0.49 | −0.97 | −0.19 | 1.10 | OK | NG |
|  | RED (PINK) GROUP INTERMEDIATE | 88.52 | 6.77 | −2.96 | 1.10 | −2.35 | 0.66 | 2.68 | OK | NG |
|  | BLUE GROUP SHALLOW | 86.90 | −4.88 | −3.11 | 1.79 | 1.89 | 0.78 | 2.72 | OK | NG |
|  | BLUE GROUP INTERMEDIATE | 85.23 | −5.19 | −4.23 | 2.99 | 3.34 | 1.70 | 4.79 | NG | NG |
|  | RED (PINK) GROUP DARK | 85.43 | 8.78 | −4.82 | 2.81 | −5.31 | 2.62 | 6.55 | NG | NG |
|  | GREEN GROUP LIGHT | 87.94 | −8.34 | 7.59 | 1.47 | 4.39 | −7.09 | 8.47 | NG | NG |
|  | BLUE GROUP DARK | 81.10 | −3.94 | −9.23 | 6.94 | 4.84 | 7.53 | 11.33 | NG | NG |
|  | BLUE GROUP INTERMEDIATE | 85.99 | −9.77 | 7.75 | 2.32 | 6.89 | −9.67 | 12.10 | NG | NG |
|  | GREEN GROUP DARK | 82.01 | −12.23 | 7.76 | 5.77 | 14.87 | −17.85 | 23.94 | NG | NG |

The test of "impression of the color difference" shown in Table 2 which is observed the samples (a square base sheet 120 of 50 mm×50 mm, a square hook fastener 110 of 30 mm×30 mm to the center of the base sheet 120) from the hook 111 side of the hook fastener 110 by the observer (subject number 50), and which is whether or not the impression such as the color difference, conducted a sensitive evaluation by the following five step. The ratio of number of evaluation in (1) or (2) was accepted as YES (OK) a sample of more than 60%.

(1) Color difference is not felt at all
(2) Color difference is not felt almost
(3) No opinion
(4) Color difference is felt little
(5) Color difference is felt clearly The test of "sense of unity" shown in the table 2 was conducted the same test with the test "fabric feeling"

than or equal to 2.23, from the viewpoint of achieving a sense of unity with the body of disposal diaper 10.

(3.3) The Light Transmittance

All measurements of the light transmittance is compliant with the standard of JIS-K7105, and using a color difference meter ($Ni_{pp}$on Denshoku Industries Co., Ltd, a flicker photometer color difference meter Z-300A). The measurement was calculated a TT value sandwiched by a turbidity meter the samples of width 5 mm and length 5 mm, and the TT value calculated was the all light transmittance of the sample (%).

The measurement was measured in the 10 samples in the each example and the comparative example, and was to the light transmittance the average value obtained by the measurement.

TABLE 3

| | | LIGHT TRANSMITTANCE | | | |
|---|---|---|---|---|---|
| | FASTENER ATTACHMENT PIECE TYPES | COLORATION (1) | COLORATION (2) | EMBOSSED NONWOVEN FABRIC (1) | EMBOSSED NONWOVEN FABRIC (2) |
| EX. 1 | 85.2% | OK | OK | OK | OK |
| EX. 2 | 61.0% | OK | OK | OK | OK |
| EX. 4 | 80.8% | OK | OK | OK | OK |
| EX. 5 | 79.8% | OK | OK | OK | OK |
| EX. 6 | 58.2% | OK | OK | NG | NG |
| COMPARATIVE EX. 3 | 49.3% | NG | NG | NG | NG |

The table 3 shows respectively a sheet of pale pink color (L=89.5, a=5.05, b=−0.98) as the base sheet 120 in a colored (1) and a sheet of pale blue color (L=85.1, a=−6.77, b=−3.89) as the base sheet 120 in a colored (2).

An embossed nonwoven fabric (1) and an embossed nonwoven fabric (2) are shows respectively, and the embossed nonwoven fabric (1) is fabric has an embossed unit of 20 g/m² basis weight, 1.0 mm diameter pattern, 20% pattern area, as the base sheet 120, and the embossed nonwoven fabric (2) is a fabric has an embossed unit of 80 g/m² basis weight, 1.5 mm diameter pattern, 35% pattern area, as the base sheet 120.

As shown in the Table 3, by setting more than 60% the light transmittance, since it can be visually confirmed watermark a texture (color and sense of fiber) of the base sheet 120 and visible a pattern 140 of the base sheet 120 (see FIG. 7) described later, thereby the effect exerted mimic can to the base sheet 120 of the hook fastener 110. The upper limit of light transmittance to such effects was can be confirmed to 85.2%.

(3.4) Bending Stiffness and Bending Resiliency

The bending characteristic of the hook fastener 110 was measured using the KES bending measuring device manufactured by Kato Tech Co., Ltd. Specifically, a B value (a bending stiffness) and a 2 HB value (a bending resiliency) were measured.

More specifically, about the KES law, its details is described on the "Standardization of evaluation of texture and analysis", Second Edition (Issued on Jul. 10, 1980, the Normalized Research Committee and texture Weighing, fabric Machinery Society of Japan). Therefore, with respect to the measurement method of the mechanical properties of each, here it describes only the measurement conditions related to the measure.

The bending characteristics was measured by as a sample a 1 cm width of a predetermined region of each sample, the sample is fixed between the chucks of 1 cm interval using the KES-FB2 of Kato Tech Corporation, and the sample is bending to the front side until +2.5 cm−1 maximum curvature, and next, sample returns to the original after bending the back side until −2.5 cm−1 maximum curvature.

The Measurement B [gf·cm²/cm] of the bending stiffness was calculated from the inclination when starting to bend on the front side and the inclination of the bending moment to curvature becomes almost constant. Also, the bending resiliency 2HB [gf·cm²/cm] was calculated from the width of the hysteresis. In addition, the bending stiffness B is obtained by averaging values of a vertical direction (longitudinal direction) and a horizontal direction (width direction) of the diaper.

TABLE 4

| | BENDING STIFFNESS (B) | BENDING RECOVERY (2HB) |
|---|---|---|
| EX. 1 | 0.0717 | 0.0703 |
| EX. 2 | 0.0099 | 0.0222 |
| EX. 3 | 0.1411 | 0.1145 |
| COMPARATIVE EX. 1 | 0.8429 | 0.3537 |
| COMPARATIVE EX. 3 | 0.2015 | 0.1763 |

The table 4 shows the test results in the example 1 to example 3, the comparative example 1 and the comparative example 3. If using the SB nonwoven fabric (60 g/m²), the value of the bending stiffness B (hereinafter, the value B) is 0.4555 gf·cm²/cm, the value of the bending resiliency 2 HB (hereinafter, the 2 HB) is 0.4575 gf·cm/cm. That is, in the example 1 to the example 3, could be confirmed that the values of the bending stiffness B and the bending resiliency 2 HB is much lower than the SB nonwoven fabric.

In the mainstream of the fabric used in clothing (an underwear), the B value is 0.005 gf·cm²/cm to 0.09 gf·cm²/cm, the 2 HB value is 0.005 gf·cm/cm to 0.06 gf·cm/cm. For example, if using the SB nonwoven fabric 35 g/m², the B value is 0.151 gf·cm²/cm, the 2 HB value is 0.124 gf·cm/cm. Therefore, the example 3 also, since the B value and the 2 HB value are low, it give to the user the impression close to the fabric.

In addition, the samples and the fabric samples in the example 1 and 2 was confirmed, in the state in which cut to width 15 mm×length 50 mm, held in the chuck of the horizontal the end unit 10 mm, the sample segment is curved in lower than the horizontal plane of the chuck. In other words, the fastening member (the hook fastener) is a sample that can be bent by its own weight sample segment, thereby when in use, the pick up member adjacent to the fastening member, the impression that can be curved like a fabric can give to the user, and a sense of unity of the fastening member can be a higher.

Further, since the sample of the comparative example 3, the thickness of the hook sheet 112 is thicker than that of the example, the distance L1 between the hooks is 120 μm which is smaller, so both of the B value and the 2 HB value are higher compared to the example.

(3.5) Surface Friction Characteristics

The surface characteristics of the hook fastener 110 was measured by the sample was set in a range of least 15 mm×30 mm at the predetermined region of each sample, and then the sample was measured by placing a test stand of a flat metal plane, using the KES-FB2 of Kato Tech Corporation. The surface roughness was measured by on the surface is applied a load of 10 gf and then the sample is crimped by the contact terminal of width 0.5 cm that wound by the piano wire of 0.5 mm diameter.

The surface friction was measured by making a sample crimp the contact surface with a force of 25 gf, by the plumb bob which consists of 20 side by side the piano wire that same as the contact terminal used for the measurement of the surface roughness. In the measurement of the surface friction and the surface roughness, the sample was 2 cm moved to horizontally at fixed speed of 0.1 cm/min.

From these measurements, an average coefficient of friction (MIU), a standard deviation (MMD) of the MIU (only the horizontal direction), and an average deviation of the surface roughness (SMD) [μm] are calculated. In order to contrast with touch of the wearing article (the disposal diaper), the inner surface of the wearing article, i.e., the contact surface to a surface skin of the wearer was measured as a surface. The table 5 shows the measurement results of the surface friction characteristics.

TABLE 5

|  | FIRST DIRECTION | | | SECOND DIRECTION | | |
| --- | --- | --- | --- | --- | --- | --- |
|  | MIU | MMD × SMD | SENSIBILITY EVALUATION | MIU | MMD × SMD | SENSIBILITY EVALUATION |
| EX. 1 | 0.13 | 0.445 | OK | 0.13 | 0.105 | OK |
| EX. 2 | 0.07 | 0.437 | OK | 0.07 | 0.178 | OK |
| COMPARATIVE EX. 1 | 0.10 | 0.724 | NG | 010 | 0.593 | OK |

※ [—] indicates that no test data are available

As shown in the table 5, the smoothness of the surface of the hook fastener 110 is represented by the accumulated value of the MMD (graininess) and the SMD (surface roughness). Usually, when the values of the MMD and the SMD are small, there is no sense of the roughness or the irregularities.

The test of "the sensitive evaluation" indicated in the table 5 is conducted the same test with the test of "the fabric feeling" described above. A standard of each stage of the five steps are as follows. The ratio of number of evaluation in (1) or (2) was accepted as YES (OK) a sample of more than 60%.

(1) Very smooth
(2) Little smooth
(3) No opinion
(4) Little graininess
(5) Very graininess Further, this time, from the sensitive evaluation by the observer, the accumulated value of both parameters and the surface smoothness are recognized that there is a correlation, without feel the smooth when the value of one of the SMD and the MMD is small.

In addition, the preferably accumulated value must meet both of the first direction (e.g., vertical direction) and the second direction (horizontal direction).

There is no problem even if the accumulated value is less than 0.1, but if the surface is too smooth, the user may illusion the hook 111 is not engaged, or the user will not know its existence in contact with the hook 111. On the other hand, if the accumulated value exceeds 0.6, it felt that there is roughness when viewed from the sensitive evaluation by the observer.

(4) Operation and Effect

According to the disposal diaper 10, the hook height H1 is set to 45 μm to 150 μm, and the hook sheet thickness T2 is set to 45 μm to 75 μm. Further, when in the L*a*b* color coordinate system, a color difference of L* is ΔL*, a color difference of a* is Δa*, and a color difference of b* is Δb*, a color difference ΔE between the hook fastener 110 and the base sheet 120 calculated using the ΔL*, the Δa* and the Δb*, is less than 5.5.

Consequently, the hook fastener 110 may have touch and physical appearance equivalent to those of nonwoven fabric and the like, other than the touch and the physical appearance of plastic as with the conventional hook fastener. That is, it is possible to significantly reduce a discomfort in the touch and the physical appearance of the hook fastener 110 and achieve a sense of unity with the body of the disposal diaper, that is the wearing article that is worn a human or a like.

The inventor(s) of the present invention has (have) found out the following three points necessary for allowing the hook fastener to have fabric feeling.

(i) Touch of hook fastener
(ii) Physical appearance of hook fastener
(iii) Relationship with base sheet Hereinafter, each point will be specifically described.

(4.1) For Fabric Feeling of Touch

If the hook sheet thickness T2 is set to be equal to or more than the above-mentioned value, touch when making contact with the hook fastener 110 causes the impression of molded plastic. That is, the hook sheet thickness T2 is set to be in the above-mentioned range, thereby reducing the bending stiffness of the hook fastener 110 and achieving flexible fabric without being buckled at the time of bending.

In addition, when the hook height H1 is high, the ribbed hook fastener 110 makes contact with the skin to stimulate the skin of a wearer. In this regard, the hook height H1 is set to be in the above-mentioned range, thereby significantly reducing stimulation (pricking and the like) to the skin of the wearer. That is, the hook height H1 is a height of a rib, which can be obtained by the knitted structure of the fabric, thereby causing rough feeling equivalent to fabric usually contacted.

Further, in the present embodiment, since the distance L1 between adjacent hooks 111 is set to 120 μm to 300 μm, such discomfort can be reduced further.

(4.2) For Fabric Feeling of Physical Appearance

When the hook height H1 is set to be in the above-mentioned range, since it is difficult to recognize that the hook 111 is pointed with the naked eye, it is possible to prevent a user of the disposal diaper 10 from feeling a discomfort (a sharp impression).

(4.3) For Fabric Feeling Obtained by a Sense of Unity with Fabric (Nonwoven Fabric)

As described above, in the disposal diaper 10 when in the L*a*b* color coordinate system, a color difference of L* is ΔL*, a color difference of a* is Δa*, and a color difference of b* is Δb*, a color difference ΔE between the hook fastener 110 and the base sheet 120 calculated using the ΔL*, the Δa* and the Δb*, is less than 5.5.

Therefore, it can achieve a sense of unity with the hook fastener 110 and the base sheet 120.

In addition, the light transmittance of from the tip side of hook 111 (the umbrella unit 111*b*) of the hook fastener 110 to the base sheet 120 side, is set to 60% to 85%. By setting the light transmittance in the above-mentioned range, state of the base sheet 120 can be visually recognized through the hook fastener 110, and the hook fastener 110 is visually recognized so that it is integrally formed with the base sheet 120 made of nonwoven fabric. Consequently, the feeling and color of the base sheet 120 can be visually recognized through the hook fastener 110, and the difference in impression by physical appearance between the hook fastener 110 and the base sheet 120 can be reduced.

Further, if the light transmittance of the hook fastener 110 is increased, the base sheet 120 is allowed to be seen through the hook fastener 110, and fine rough feeling due to the hook fastener 110 occurs, since sense such as surface-contacting the skin to a film disappears, an adverse impression to the skin can be reduced. In addition, the color difference between the hook fastener 110 and the base sheet 120 is set to be in the above-mentioned range, thereby achieving a sense of unity of the physical appearance between the hook fastener 110 and the base sheet 120.

Since the hook height H1 and the boundary between the hook fastener 110 and the base sheet 120 due to the hook sheet thicknesses T2 causes a discomfort for other portions of the disposal diaper 10, the hook height H1 and the thicknesses (the total thickness T1 and the hook sheet thickness T2) of the hook fastener 110 and the base sheet 120 are set to be in the above-mentioned range, thereby preventing unevenness between the hook fastener 110 and the base sheet 120 from being felt, and achieving a sense of unity of the touch between the hook fastener 110 and the base sheet 120. In addition, since the difference in the thicknesses of the hook fastener 110 and the base sheet 120 is small, difference in stiffness therebetween is also small. Since the hook fastener 110 and the base sheet 120 are prevented from being bent about the boundary therebetween, it is possible to achieve a sense of unity of the physical appearance therebetween.

(5) Other Embodiments

So far, the present invention is disclosed through the above embodiment. However, it should not be interpreted that the statements and drawings constituting a part of the present disclosure limit the present invention. Various alternative embodiments, examples and operating technologies will be apparent to those skilled in the art after reading the present disclosure.

Figure 7:
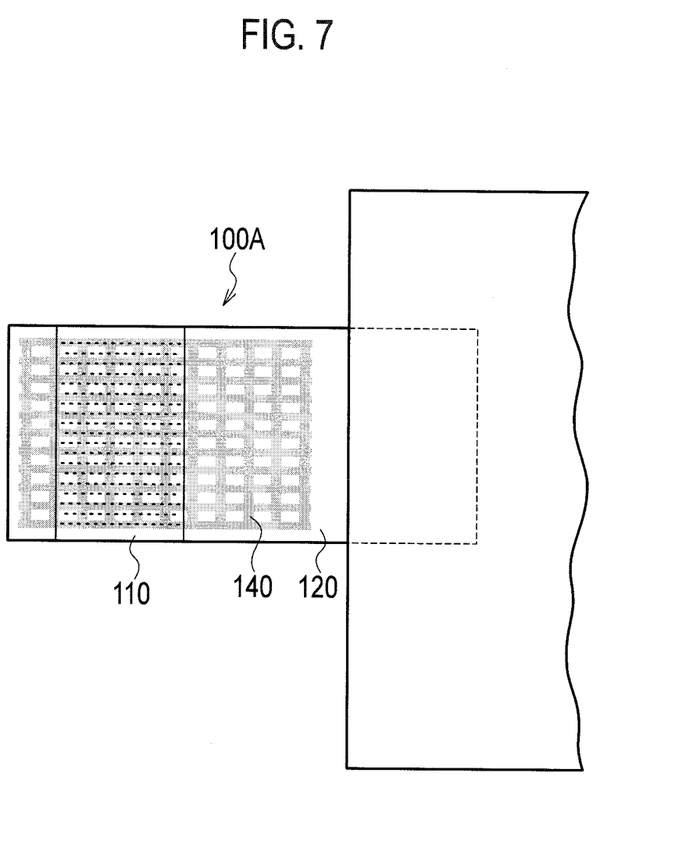
FIG. 7 is a plan view of a fastening segment 100A according to a modification of the present invention.

For example, the embodiment of the present invention can be modified as follows. FIG. 7 is a plan view of a fastening segment 100A according to a modification of the present invention. As illustrated in FIG. 7, in the fastening segment 100A, a predetermined pattern 140 by a design, the texture pattern shape in the example shown in FIG. 7 are provided on the surface of the hook fastener 110 side of the base sheet 120. The pattern 140 is continuously provided from a formation area of the hook fastener 110 of the base sheet 120 to a non-formation area of the hook fastener 110.

As described above, since the light transmittance of the hook fastener 110 is set to 60% to 85%, it is possible to visually recognize the pattern 140 provided on the base sheet 120 through the hook fastener 110. Consequently, a sense of unity of the physical appearance between the hook fastener 110 and the base sheet 120 can be further increased. In addition, the pattern 140 may be various patterns, or may be obtained by embossing, instead of a design.

Figure 8:
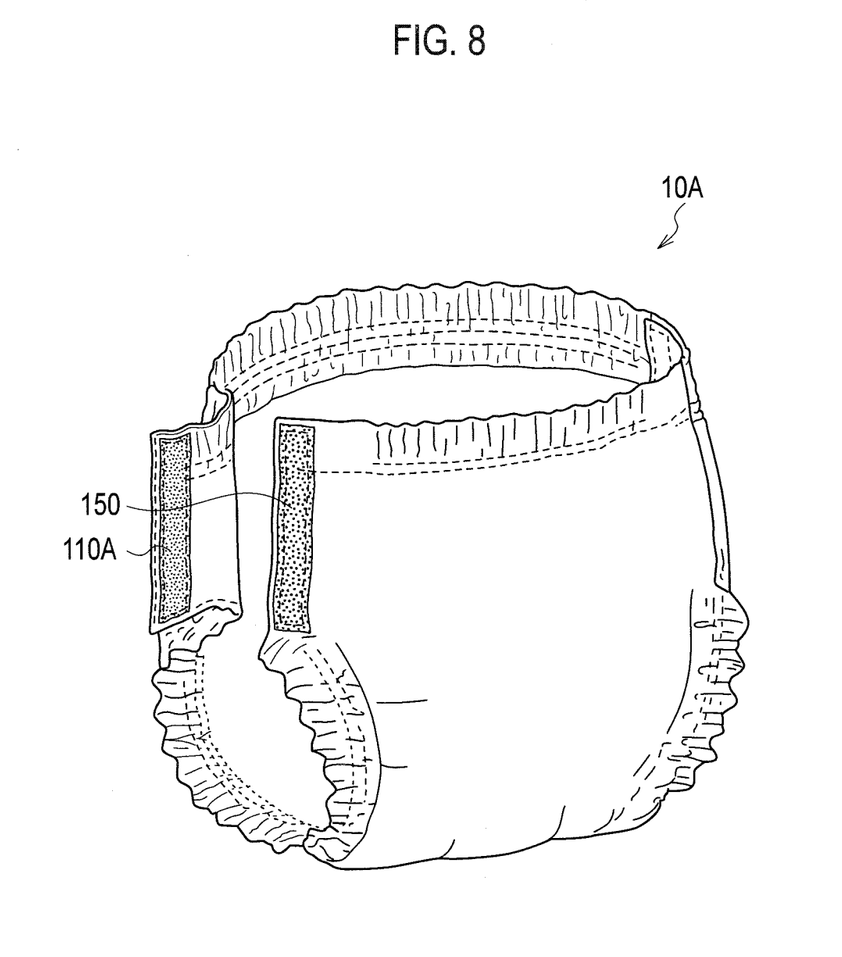
FIG. 8 is a schematic perspective view of a disposal diaper 10A according to the modification of the present invention.

FIG. 8 is a schematic perspective view of a disposal diaper 10A according to the modification of the present invention.

As illustrated in FIG. 8, the disposal diaper 10A includes a hook fastener 110A and a target tape 150. The disposal diaper 10A is a pants-type disposal diaper in which a front waistline unit is joined to a rear waistline unit. In the disposal diaper 10A, the hook fastener 110A and the target tape 150 are provided at a joint unit (a side unit) of one of the front waistline unit and the rear waistline unit, and the side unit is detachable.

The hook fastener 110A may have approximately the same configuration as that of the above-mentioned fastening segment 100. Further, the target tape 150 includes a female member of the hook fastener with which the hook portion of the hook fastener 100A is engaged. As the target tape 150, a material well known in the art can be used.

So far, in the above-mentioned embodiments, the disposal diaper 10 has been described as an example. However, the application range of the present invention is not limited to the disposal diaper. That is, the present invention can also be applied to other disposal wearing articles, for example, a wing unit and the like of a sanitary napkin. Further, the application range of the present invention which is not limited to the disposal wearing article, and which is worn to the human and the animal (the pets) or the like, and the present invention can be suitably used to the wearing articles such as clothing made of nonwoven fabric or the like.

Thus, needless to say, the present invention includes various embodiments not described herein. Therefore, the technical range of the present invention is to be defined only by the inventive specific matter according to the adequate scope of inventions from the above description.

This application is based on Japanese Patent Application No. 2011-203456 filed with the Japan Patent Office on Sep. 16, 2011, the entire content of which is hereby incorporated by reference.

INDUSTRIAL APPLICABILITY

According the characteristics of the present invention, it is possible to provide a fastening member and a fastening segment, which is capable of significantly reducing a discomfort in touch and physical appearance and achieving a sense of unity with the body of the wearing article of the disposal diaper or the like.

REFERENCE SIGNS LIST

10 . . . Disposal diaper
20 . . . Front waistline unit
30 . . . Crotch unit
35 . . . Absorber
40 . . . Rear waistline unit
100, 100A . . . Fastening segment
110, 110A . . . Hook fastener
111 . . . Hook
111*a* . . . Pillar unit
111*b* . . . Umbrella unit
112 . . . Hook sheet
120 . . . Base sheet
120*a* . . . Joint portion
130 . . . Adhesive layer
140 . . . Pattern
150 . . . Target tape

The invention claimed is:

1. A fastening member for a wearing article, the wearing article having a base sheet configured to be fixed to the fastening member, said fastening member comprising:
   a plurality of hooks; and
   a planar hook sheet provided with the plurality of hooks, wherein
   a height of each of the plurality of hooks is 45 μm to 150 μm,
   a thickness of the hook sheet is 45 μm to 75 μm, and
   in an L*a*b* color coordinate system,
      a color difference of L* is ΔL*,
      a color difference of a* is Δa*,
      a color difference of b* is Δb*, and
      a color difference ΔE between the fastening member and the base sheet, calculated according to a formula: $\Delta E = \sqrt{\Delta L^{*2} + \Delta a^{*2} + \Delta b^{*2}}$, is less than 5.5.

2. The fastening member according to claim 1, wherein a light transmittance of the fastening member, in a direction from a tip of each of the plurality of hooks toward the hook sheet, is 60% to 85%.

3. The fastening member according to claim 1, wherein a distance between adjacent hooks of the plurality of the hooks is 120 μm to 300 μm.

4. The fastening member according to claim 1, wherein an accumulated value of (i) a standard deviation of an average coefficient of friction of the fastening member and (ii) an average deviation of the average coefficient of friction is 0.10 to 0.45.

5. The fastening member according to claim 1, wherein a bending stiffness of the fastening member in a first direction along a surface of the fastening member and a bending stiffness of the fastening member in a second direction perpendicular to the first direction along the surface of the fastening member are equal to or less than 0.142 gf·cm²/cm.

6. The fastening member according to claim 5, wherein a bending resiliency of the fastening member in the first direction or in the second direction is equal to or less than 0.1145 gf·cm/cm.

7. The fastening member according to claim 1, wherein the base sheet includes a nonwoven fabric, and a basis weight of an entirety of the nonwoven fabric is 10 to 100 g/m².

8. The fastening member according to claim 7, wherein a thickness of the entirety of the nonwoven fabric is 50 μm to 600 μm.

9. The fastening member according to claim 1, wherein a bending stiffness of the fastening member in a first direction along a surface of the fastening member and a bending stiffness of the fastening member in a second direction perpendicular to the first direction along the surface of the fastening member are equal to or less than 0.072 gf·cm²/cm.

10. The fastening member according to claim 1, wherein the color difference ΔE between the fastening member and the base sheet is in a range of 0.29 and 5.5.

11. A fastening segment, comprising:
    a fastening member having a plurality of hooks and a planar hook sheet provided with the plurality of hooks,
    a base sheet fixed to the fastening member,
    wherein
    a height of each of the plurality of hooks is 45 μm to 150 μm,
    a thickness of the hook sheet is 45 μm to 75 μm, and
    in an L*a*b* color coordinate system,
       a color difference of L* is ΔL*,
       a color difference of a* is Δa*,
       a color difference of b* is Δb*, and
       a color difference ΔE between the fastening member and the base sheet, calculated according to a formula: $\Delta E = \sqrt{\Delta L^{*2} + \Delta a^{*2} + \Delta b^{*2}}$, is less than 5.5.

12. The fastening segment according to claim 11, wherein
    the base sheet has a surface to which the fastening member is attached, said surface including a predetermined pattern including at least one of a predetermined design, a pattern, and an emboss,
    the fastening member has a formation area where the plurality of hooks and the hook sheet are formed, and a reminder defining a non-formation area, and
    the predetermined pattern continuously extends from the formation area of the fastening member to the non-formation area of the fastening member.

13. The fastening segment according to claim 11, wherein a light transmittance of the fastening member, in a direction from a tip of each of the plurality of hooks toward the hook sheet, is 60% to 85%.

14. The fastening segment according to claim 11, wherein a distance between adjacent hooks of the plurality of the hooks is 120 μm to 300 μm.

15. The fastening segment according to claim 11, wherein an accumulated value of (i) a standard deviation of an average coefficient of friction of the fastening member and (ii) an average deviation of the average coefficient of friction is 0.10 to 0.45.

16. The fastening segment according to claim 11, wherein a bending stiffness of the fastening member in a first direction along a surface of the fastening member and a bending stiffness of the fastening member in a second direction perpendicular to the first direction along the surface of the fastening member are equal to or less than 0.142 gf·cm²/cm.

17. The fastening segment according to claim 16, wherein a bending resiliency of the fastening member in the first direction or in the second direction is equal to or less than 0.1145 gf·cm/cm.

18. The fastening segment according to claim 11, wherein the base sheet includes a nonwoven fabric, and a basis weight of an entirety of the nonwoven fabric is 10 to 100 g/m².

19. The fastening segment according to claim 18, wherein a thickness of the entirety of the nonwoven fabric is 50 μm to 600 μm.

20. The fastening segment according to claim 11, wherein a bending stiffness of the fastening member in a first direction along a surface of the fastening member and a bending stiffness of the fastening member in a second direction perpendicular to the first direction along the surface of the fastening member are equal to or less than 0.072 gf·cm²/cm.

21. The fastening segment according to claim 11, wherein the color difference ΔE between the fastening member and the base sheet is in a range of 0.29 and 5.5.

* * * * *